United States Patent [19]

Cunningham

[11] Patent Number: 4,506,541
[45] Date of Patent: Mar. 26, 1985

[54] MEASUREMENT OF BULK DENSITY OF PARTICULATE MATERIALS

[75] Inventor: Jock B. Cunningham, Mount Isa, Australia

[73] Assignee: Mount Isa Mines Limited, Australia

[21] Appl. No.: 438,882

[22] PCT Filed: Mar. 16, 1982

[86] PCT No.: PCT/AU82/00028
§ 371 Date: Oct. 15, 1982
§ 102(e) Date: Oct. 15, 1982

[87] PCT Pub. No.: WO82/03273
PCT Pub. Date: Sep. 30, 1982

[30] Foreign Application Priority Data

Mar. 16, 1981 [AU] Australia .............. PE8014

[51] Int. Cl.$^3$ .............................. G01N 9/24
[52] U.S. Cl. ................ 73/32 R; 73/861.02; 250/308; 250/358.1
[58] Field of Search ............ 73/861.05, 30, 32 R; 250/356.1, 356.2, 308, 358.1; 376/246; 356/338

[56] References Cited

U.S. PATENT DOCUMENTS

| 2,925,007 | 2/1960 | Silver | 250/356.1 X |
| 3,300,640 | 1/1967 | Eubank | 73/30 |
| 3,654,109 | 4/1972 | Hohl | 250/356.1 X |
| 4,053,229 | 10/1977 | McCluney | 356/338 |
| 4,072,421 | 2/1978 | Coyne | 356/338 X |
| 4,178,103 | 12/1979 | Wallace | 356/338 X |
| 4,210,809 | 7/1980 | Pelavin | 250/356.1 X |
| 4,282,433 | 8/1981 | Löffel | 250/356.2 |

Primary Examiner—Charles A. Ruehl
Assistant Examiner—Vincent P. Kovalick
Attorney, Agent, or Firm—Darby & Darby

[57] ABSTRACT

Apparatus for measuring the bulk density and mass flow rate of pulverized coal entrained in air along a duct 6 comprises beta radiation source means 7, radiation detection means 8 and a shield 9 to intercept direct radiation falling on the detector means which thereby measures the diffuse radiation scattered by the coal particles. That measurement plus a signal indicating linear coal particle speed is fed to a data processor which calculates the bulk density and mass flow rate.

6 Claims, 5 Drawing Figures

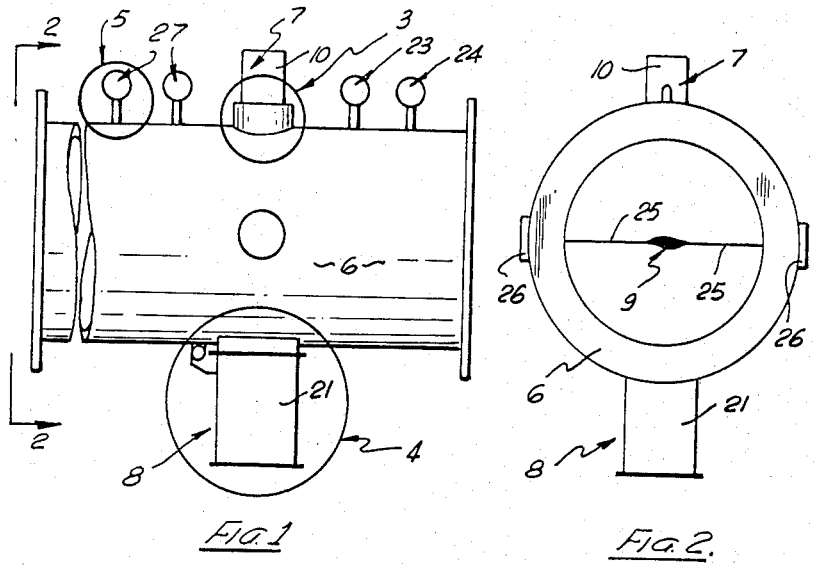
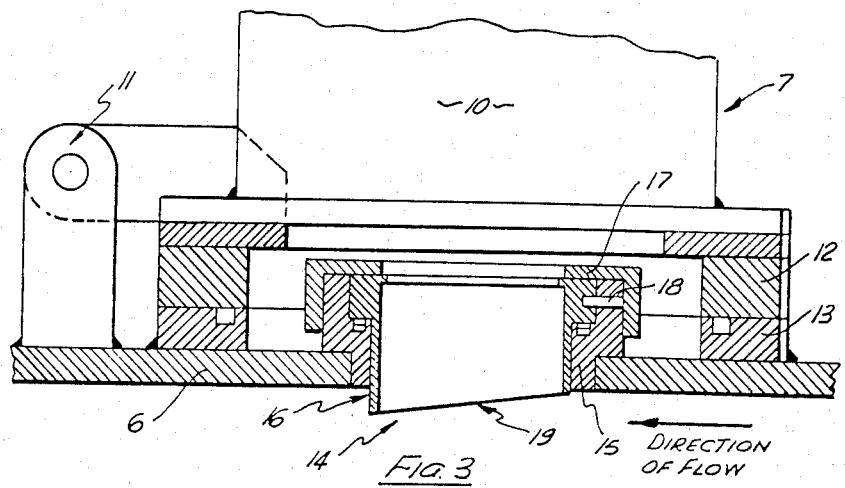

MEASUREMENT OF BULK DENSITY OF PARTICULATE MATERIALS

This invention relates to the determination of the combined bulk density of material being in the form of either a gas, a vapour, an aerosol, or particulate solids suspended in a gas (for example; dust). The term combined bulk density refers to the density of the material when viewed as a whole. For example, in the case of suspended solids in a gas, cognizance is taken of the volume between the particles of material as if it were part of the composition.

The invention was devised primarily to monitor the combined bulk density of powdered coal in flow streams of coal entrained with air and/or other gases. Thus, the invention is described primarily with reference to that application but it will be appreciated that it is applicable to the measurement of the combined bulk density of other materials generally in the aforementioned form.

Hitherto, one technique for determining the combined bulk density of such material, has been to beam beta radiation from an isotope source through a predetermined thickness of the material to a radiation detector.

The extent to which the beam of radiation is attenuated by the material is determined by the detector which detects the residual radiation of the beam which is related to the bulk density of the material. In any particular application the calibration of the apparatus is either:

(1) assumed to follow the classical attenuation relationship $$I = I_0 e^{-\mu \rho}$$

where I is the residual radiation intensity;
$I_0$ is the radiation intensity at a particular reference combined bulk density (often zero);
$\rho$ is the combined bulk density and
$\mu$ is mass attenuation coefficient or calibration constant; OR (2) determined against samples of the material of which the bulk density has been determined by more fundamental but less convenient measurement.

The maximum sensitivity of such an apparatus is obtained using the aforementioned classical relationship. This is only true, however, if a collimator is used on either the source and/or detector to minimise the amount of scattered radiation being detected. Sensitivity varies according to the quality of the collimator and rarely could the classical equation be used without modification by a more practical method of calibration. In addition, because of the inevitable inefficiency of collimators, some of the residual radiation that would otherwise follow the classical attenuation relationship is absorbed by the collimator and thus is not detected. This in turn reduces the precision with which the determination of combined bulk density could be made within a certain time period according to the theory of radiation detecting statistics and assuming all other aspects of the apparatus remain unchanged.

The foregoing technique suffers from the fact that the narrow beam of radiation intersects only a small sample of the material and thus is liable to error if that sample is not representative of the material as a whole.

The present invention seeks to overcome the above indicated disadvantages by very simple means.

According to the invention a bulk density measuring apparatus is provided comprising uncollimated radiation source means, uncollimated radiation detector means spaced from said source means to measure radiation received therefrom, containment means for the material of which the density is to be determined such that a charge of the material within said containment means occupies the space between the source means and detector means, and a radiation opaque shield positioned to prevent direct radiation from the source means reaching the detector means.

Thus instead of detecting the intensity of the original radiation less the attenuated radiation, the detector of apparatus in accordance with the invention detects only scattered radiation and, due to the diffuse scatter path, the radiation reaching the detector has been affected by a much larger volume of the material than is the case in prior art apparatus.

Once again the apparatus is calibrated before use against samples of a material of predetermined bulk density.

In preferred embodiments of the invention the radiation source and detector are mounted externally of the containment means and the radiation travels from one to the other through radiation transparent windows in the wall or walls of the containment means.

In some instances, the containment means may be a duct through which a stream of the material is caused to flow and in such instances the apparatus may be associated with means for determining the speed of flow thereby enabling the mass flow rate to be calculated. For preference, the instantaneous readings indicative of bulk density and flow speed are fed to a data processor which calculates the instantaneous mass flow rate and which may integrate the flow rate values to provide an indication of the total mass flow in a predetermined time. It will be apparent to those skilled in the art that such a data processor may also be used to control the means establishing the flow so as to maintain a constant mass flow rate.

As indicated earlier the invention was developed primarily to measure the combined bulk density of a material consisting of coal particles (pulverised coal) suspended in an air stream within a duct. This mixture may be supplied from a coal pulveriser to a furnace as a source of fuel. Alternatively the bulk density of the coal particles (including moisture) alone may be determined, that is, excluding as part of the material the voids between the particles that are otherwise filled with gas. This is achieved by subtracting from the measured combined bulk density, the density of the air determined from a measurement of the air pressure and temperature. Furthermore, the mass flow of the pulverised coal may be determined by multiplying the bulk density of the coal by the volume rate at which the coal flows through the duct. The volume rate of flow may be determined by calculating the product of the linear rate of flow and the cross-sectional area of the duct. The linear flow rate may be determined by measuring the transit time of the coal between two points set apart along the direction of flow. This may be achieved by detecting the frictionally induced electric charge normally occurring on particles of pulverised coal and issuing a signal proportional to the charge at each point. The time delay between the two signals and hence the linear speed of the coal is determined by cross-correlating the two signals.

By way of example a preferred embodiment of the invention is now described with reference to the accompanying drawings.

FIG. 1 is a diagrammatic side elevation of a bulk density measuring apparatus according to the invention.

FIG. 2 is a diagrammatic end view of the apparatus of FIG. 1 when viewed in the direction of the arrows 2—2 in that figure.

FIG. 3 is a sectional view of a window assembly being a component of the apparatus of FIG. 1 disposed within the boundary marked 3 in that figure drawn to a larger scale.

Referring initially to FIGS. 1 and 2, the illustrated apparatus comprises containment means in the form of a tubular duct 6 adapted to convey a stream of pulverised coal entrained in air, radiation source means 7, radiation detector means 8 and a radiation opaque shield 9 within the duct 6 positioned to prevent radiation travelling directly from the source means 7 to the detector means 8 but permitting diffused radiation scattered by the coal particles to reach the detector means 8.

Figure 4:
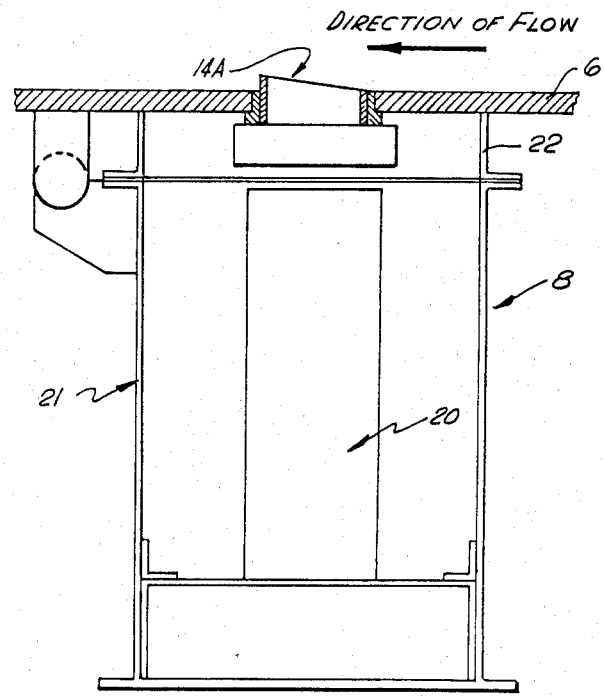
FIG. 4 is a sectional view of a radiation detector means being a component of the apparatus of FIG. 1 disposed within the boundary marked 4 in that figure drawn to a larger scale.
Figure 5:
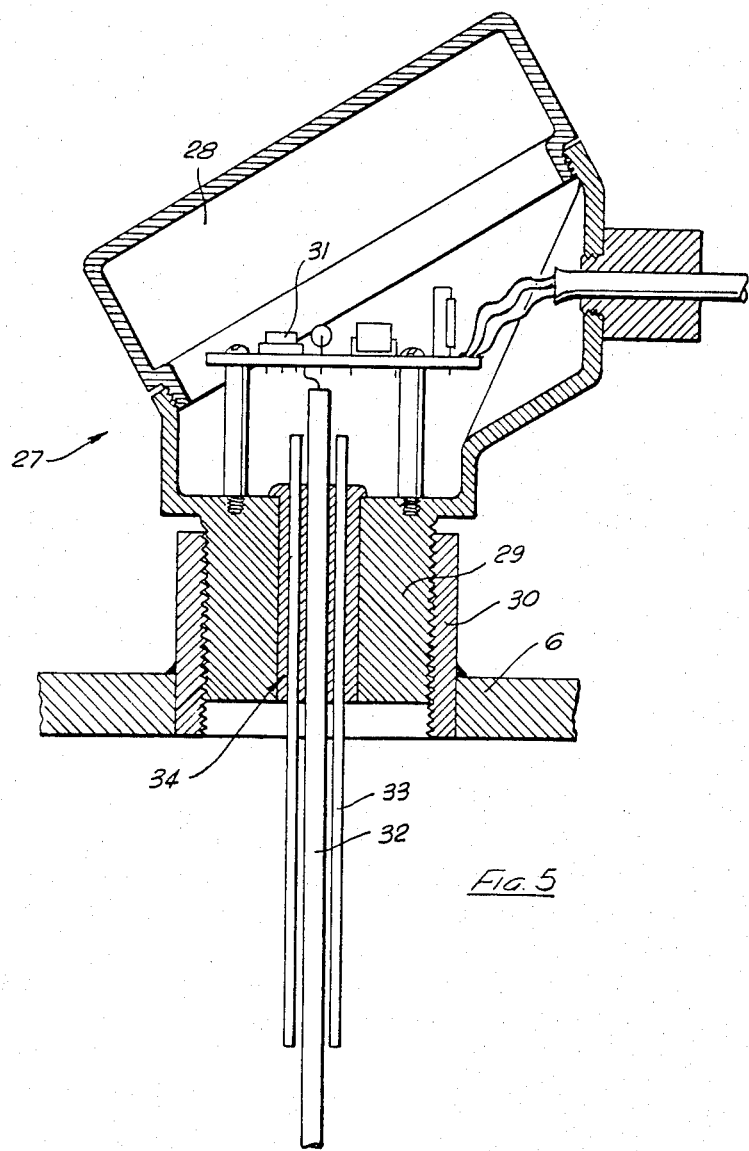
FIG. 5 is a sectional view of an electrode probe assembly being a component of the apparatus of FIG. 1 disposed within the boundry marked 5 in that figure drawn to a larger scale.

The radiation penetrates the duct wall by way of two window assemblies respectively associated with the source means 7 and detector means 8. The window assemblies do not appear in FIG. 1 or 2 but are described more particularly below with reference to FIGS. 3 and 4.

The radiation source means 7 may comprise a source of beta radiation, for example 3700 giga becquerel of strontium-90 (not shown) housed within a lead filled steel case 10 hingedly mounted at 11 on the duct 6. A sealing flange 12 rimming the mouth of the steel case 10 makes sealing engagement with a collar 13 encompassing a window assembly 14 in the wall of the duct 6.

The radiation source means are in themselves conventional in nature and their detailed structure is not germane to this invention. Depending upon the country in which the apparatus is to be used there will be safety codes and standards which would have to be met. Generally speaking, such codes would require the source to be movable within the case 10 from a position wherein it issues radiation through the mouth of the case to another position in which the radiation impinges on a beam stop. The beam stop serves to absorb beta radiation with the minimum production of Bremsstrahlung radiation and to that end may be made of nylon. Furthermore, the means securing the case 10 in the position shown in FIG. 3 would be interlocked, preferably mechanically, with the means for moving the radiation source within the case 10 to prevent the case being swung into the open position except when the radiation is issued into the beam stop.

The window assembly 14 comprises a spigot 15 encircling an opening in the wall of the duct 6, a removable window frame 16, a ring lock-nut 17, a locating pin 18 which ensures that the frame 16 is positioned in a predetermined angular alignment and a metal foil windowpane 19 closing one end of the frame 16. The windowpane 19 may, for example, be of tungsten, steel or other abrasion resistant metal.

It is important that the angle between the foil windowpane 19 and the wall of the duct 6, as measured in the centre plane of the duct intersecting the windowpane, is chosen so that the upstream edge of the windowpane is somewhat more in-board of the duct wall than is the downstream edge. The latter is somewhat out-board of the duct wall, that is, in-board of the duct itself. If the foil windowpane were to lie substantially in the plane of the duct wall or, in the event of a circular duct, if it were substantially tangential thereto, the coal dust would settle on the foil to form an absorbing layer detracting from the beta radiation through the window and thereby rendering the density measurement inaccurate.

In practice the angle of the foil windowpane 19 is adjusted so that it is just large enough for the gas stream to prevent accretion of dust on the foil yet is small enough to avoid unacceptable wear of the foil by coal particles scrubbing against it. If the angle of divergence of the foil from the duct wall is small enough having regard to the mass of the individual coal particles and the velocity of movement of the entraining air stream, the change in direction of the stream line of air as it moves from the pipe wall over the windowpane is not so abrupt as to prevent it changing the direction of movement of the suspended coal particles. If the angle is too large the momentum of the coal particles carries them out of the stream line allowing them to scrub against the foil windowpane.

In practice in any particular installation, it is a simple matter of trial and error to arrive at an optimum angle for the divergence of the windowpane 19 from the plane of the wall.

A similar window assembly 14A (see FIG. 4) admits radiation to a radiation detector 20 and the two window assemblies 14 and 14A are mounted directly opposite each other along a diameter of the duct.

The detector 20 is a conventional item in itself and several suitable detectors are offered for sale by manufacturers thereof. For example, it may be a type 663/C with an EMI 9757 photomultiplier (type D phosphor) and a 10 mm thick plastic scintillator (KOCH-Light type KL211).

The detector 20 and associated preamplifier (not shown) is enclosed in a steel case 21 which closes onto a flange 22 encompassing the window assembly 14A. Cooling air may be supplied automatically into the case 21 and around the detector 20 when the ambient temperature within the detector 20 exceeds the specifications for the detector.

Mounted nearby is a thermometer 23 and a pressure gauge 24 to measure the temperature and pressure of the air within the duct from which the air density can be calculated and then subtracted from the combined bulk density as determined by the embodiment of the invention now being described to yield the bulk density of the coal (be it wet or otherwise combined with material other than air).

The opaque radiation shield 9 is suspended in the duct in line between the window assemblies 14 and 14A such that it absorbs all radiation issued from the source which would otherwise impinge directly on the detector. The shield 9 is supported on two spring steel wires 25 or alternatively (not shown) on a length of rigid steel attached at one point to the duct. The latter method of support can be used if an unacceptable wear life is achieved by the spring steel wires 25. The shield 9 is bevelled at its edges in order to assist in streamlining.

The wires 25 are secured to anchorages 26, which preferably include adjusting screws (not shown) enabling the shield 9 to be centered and enabling the wires 25 to be tensioned.

In order to derive two signals representing the electric charge of the coal dust at two points spaced apart in the direction of flow, electrode probes assemblies are inserted into the duct at said points. Each probe assembly 27 comprises a housing 28, having a plug-like base 29 adapted to be screwed into a threaded spigot 30 encircling an opening in the wall of the duct 6. The housing 28 holds an amplifier 31 connected to a conductive electrode 32 made from a wear resistant material, such as for example silver steel. The electrode 32 is insulated from the base 29 by means of a ceramic tube 33 and the layers 34 of epoxy resin cement. Charge relative to the pipe wall is both induced and deposited onto the electrode as the coal passes nearby and collides therewith. This charge is amplified from each probe and supplied to an electronic circuit which determines, by means of a cross-correlation technique, the time delay between the two signals which is the transit time of the coal dust between the said points. The flow speed of the coal is calculated from this measurement.

All signals from the apparatus including flow speed, air temperature and pressure, and the detected radiation intensity are supplied to a data processor which calculates the coal mass flow by the aforementioned technique.

The apparatus may be calibrated in the following manner. The apparatus is constructed as an instrument on a five meter length of duct similar to the duct to be used to carry the pulverised fuel. As a first means of calibration the said five meter length of duct is sealed at its ends and filled with air to various pressures. At each pressure the air density is calculated with regard to air temperature and air pressure, and the radiation intensity measured in accordance with this invention and related to the air density. An empirical calibration equation is determined from this data.

The relationship is of the form $$I = A\rho^2 - A\rho_0\rho$$

where I is the detected radiation intensity, A is a calibration constant pertaining to the selection of a particular equation from a family of equations having the same roots, $\rho$ is the combined bulk density and $\rho_0$ is another calibration constant pertaining to the range of combined bulk densities covered by the instrument. This is influenced by the relative geometries of the radiation source, windows to the duct, opaque radiation shield, radiation detector and the material of which the combined bulk density is to be determined.

As a second means of calibration the apparatus is installed as described and a known mass of coal is passed along the duct. At the same time the coal mass flow measured by the device using the aforementioned first means of calibration is integrated and compared with the mass known to have passed over the period of integration. The calibration equation is modified and the said precedure is repeated until the desired accuracy is obtained. Indeed for simple control of a coal mill and furnace the second means of calibration may not be necessary.

The claims defining the invention are as follows.

I claim:

1. A bulk density measuring apparatus comprising:
   uncollimated radiation source means;
   uncollimated radiation detector means spaced from said source means to measure radiation received therefrom;
   containment means for the material of which the density is to be determined such that a charge of the material within said containment means occupies the space between the source means and detector means, said containment means comprising a duct along which said material is caused to flow, said radiation means and said radiation source means being mounted externally of said containment means;
   a radiation opaque shield positioned to prevent direct radiation from the source means reaching the detector means; and
   radiation transparent windowpanes respectively associated with the detector means and source means, the radiation entering and leaving the containment means through said windowpanes, each said windowpane being inclined relative to the direction of flow with its downstream edge more outboard of the duct wall than its upstream edge.

2. Apparatus according to claim 1 in association with a data processor connected to receive data from said detector means and able to compute the bulk density.

3. Apparatus according to claim 1 including means to measure the flow speed of the material.

4. Apparatus according to claim 3 in association with a data processor connected to receive data from said detector means and said means to measure the flow speed and able to calculate the mass flow rate of the material in a predetermined time.

5. Apparatus according to claim 3 including means to measure the pressure and temperature of a gaseous component of said material.

6. Apparatus according to claim 5 in association with a data processor connected to receive data from said detector means, said means to measure the flow speed and said means to measure pressure and temperature and able to calculate the mass flow rate of any non-gaseous components of the material.

* * * * *